US00PP32543P3

(12) United States Plant Patent
van Zoest

(10) Patent No.: US PP32,543 P3
(45) Date of Patent: Dec. 1, 2020

(54) ***CLEMATIS* PLANT NAMED 'ZO08160'**

(50) Latin Name: ***Clematis* hybrid**
Varietal Denomination: Zo08160

(71) Applicant: J. van Zoest Beheer B.V., Boskoop (NL)

(72) Inventor: Jan van Zoest, Boskoop (NL)

(73) Assignee: J. VAN ZOEST BEHEER B.V., Boskoop (NL)

( * ) Notice: Subject to any disclaimer, the term of this patent is extended or adjusted under 35 U.S.C. 154(b) by 0 days.

(21) Appl. No.: 16/602,140

(22) Filed: Aug. 13, 2019

(65) Prior Publication Data

US 2020/0305321 P1 Sep. 24, 2020

(30) Foreign Application Priority Data

Mar. 18, 2019 (QZ) ..... PBR 2019/0725

(51) Int. Cl.
*A01H 5/02* (2018.01)
*A01H 6/72* (2018.01)

(52) U.S. Cl.
USPC ..... Plt./228
CPC ..... *A01H 6/72* (2018.05)

(58) Field of Classification Search
USPC ..... Plt./226, 228
See application file for complete search history.

(56) References Cited

PUBLICATIONS

Horticulture Connected, Novelties at Plantarium 2018—Part 3. https://horticultureconnected.ie/news/ornamentals/novelties-at-plantarium-2018-part-3/. 4 pages (Year: 2018).*

* cited by examiner

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of hybrid *Clematis* plant named 'Zo08160' that is characterized by its very free flowering habit in spring from old wood and in late spring and summer from young shoots, its low growing climbing habit, its light lilac colored flowers with pale yellow stamens, and its cold hardiness at least to U.S.D.A. Zone 6.

2 Drawing Sheets

Botanical classification: *Clematis* hybrid.
Variety denomination: 'Zo08160'.

CROSS REFERENCE TO A RELATED APPLICATION

This application claims priority to European Community Plant Variety Office (CPVO) Plant Breeder's Rights Application No. 2019/0725 filed on Mar. 18, 2019, the entire contents of which is incorporated by reference herein.

BACKGROUND OF THE INVENTION

The present invention relates to a new and distinct cultivar of *Clematis* of hybrid origin and will be referred to hereafter by its cultivar name 'Zo08160'. 'Zo08160' is an herbaceous perennial grown for use as a landscape plant.

The new Invention arose from an ongoing controlled breeding program in Boskoop, The Netherlands. The objective of the breeding program is to develop hybrid cultivars of *Clematis* with unique and superior garden attributes. In particular, to develop cultivars that are free flowering from old wood in spring and free flowering on young shoots in later spring.

The Inventor made a cross in 2004 between an unnamed proprietary plant in the Inventor's breeding program, reference no. 19960250 as the female parent and reference no. 19990055 as the male parent. The Inventor selected 'Zo08160' in 2008, as a single unique plant amongst the seedlings that resulted from the above cross.

Asexual propagation of the new cultivar was first accomplished by softwood stem cuttings under the direction of the Inventor in 2008 in Boskoop, The Netherlands. Asexual propagation by softwood stem cutting has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish *Clematis* 'Zo08160' as a unique cultivar of *Clematis*.

1. 'Zo08160' exhibits a very free flowering habit in spring from old wood and in late spring and summer from young shoots.
2. 'Zo08160' exhibits a low growing climbing habit.
3. 'Zo08160' exhibits a light lilac colored flowers with pale yellow stamens.
4. 'Zo08160' exhibits cold hardiness at least to U.S.D.A. Zone 6.

The female parent of 'Zo08160' differs from 'Zo08160' in having double flowers in the spring, flower colors that are pink with dark purple stripes and flowers that are smaller in size. The male parent of 'Zo08160' differs from 'Zo08160' in having flowers that are white in color and much larger in size. 'Zo08160' can be most closely compared to the *Clema-*

*tis* cultivars 'General Sikorski' (not patented) and 'Paola' (not patented). Both are similar to 'Zo08160' in having flower color and plant habit. 'General Sikorski' differs from 'Zo08160' in having flat tepal margins and filament bases that are pale violet in color. 'Paola' differs from 'Zo08160' in having flat tepal margins and spring flowers that are double or semi-double.

STATEMENT DESIGNATING A GRACE PERIOD UNDER 102(b)(1)

The Applicant claims prior art exemption under 35 U.S.C. 102(b)(1) for disclosure and/or sales prior to the filing date but less than one year prior to the effective filing date if need be. Information about the claimed plant was obtained from a direct or indirect disclosure from the Inventor; including but not limited to disclosures on websites by J Van Zoest, Thorncroft, Taylors *Clematis*, Dobbies, and *Clematis* on the web.

BRIEF DESCRIPTION OF THE DRAWINGS

The accompanying colored photographs illustrate the overall appearance and distinct characteristics of the new *Clematis*. The photographs were taken of a two-year-old plant as grown outdoors in a 2-liter rose container in Boskoop, The Netherlands.

The photograph in FIG. 1 provides a view of 'Zo08160' in bloom in spring.

Figure 1:
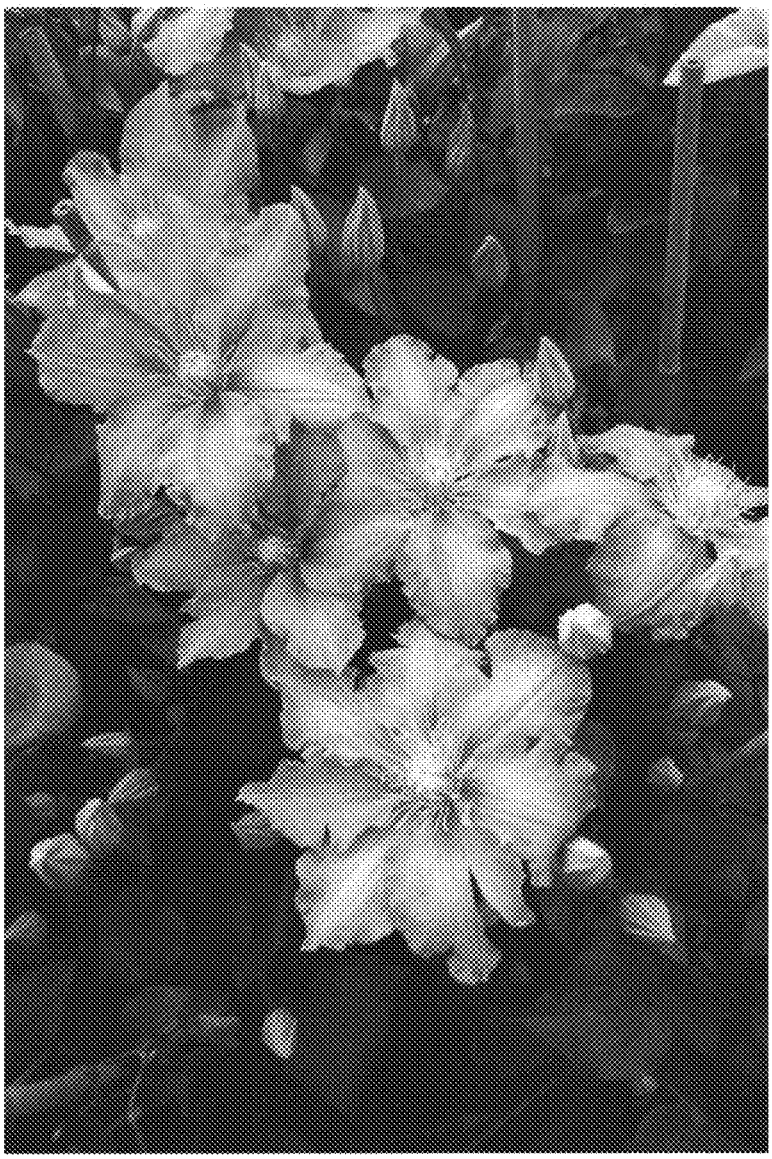
Figure 2:
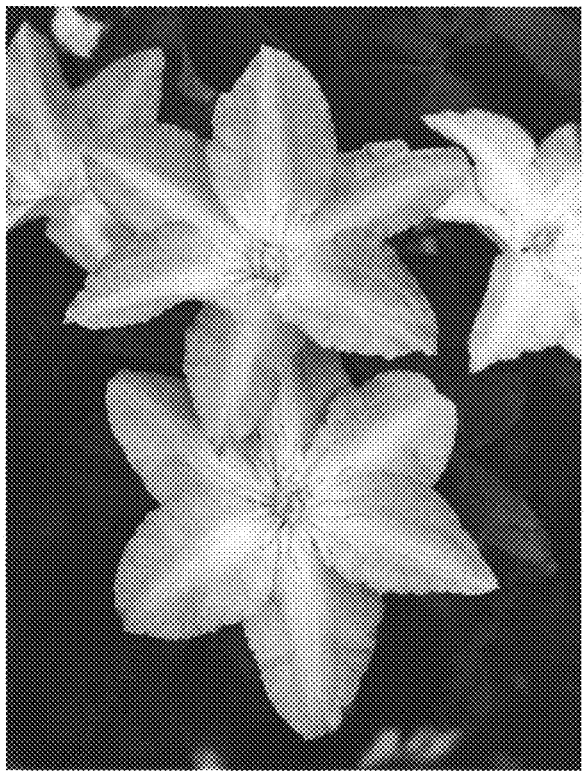

The photograph in FIG. 2 provides a close-up view of the summer flowers 'Zo08160'.

Figure 3:
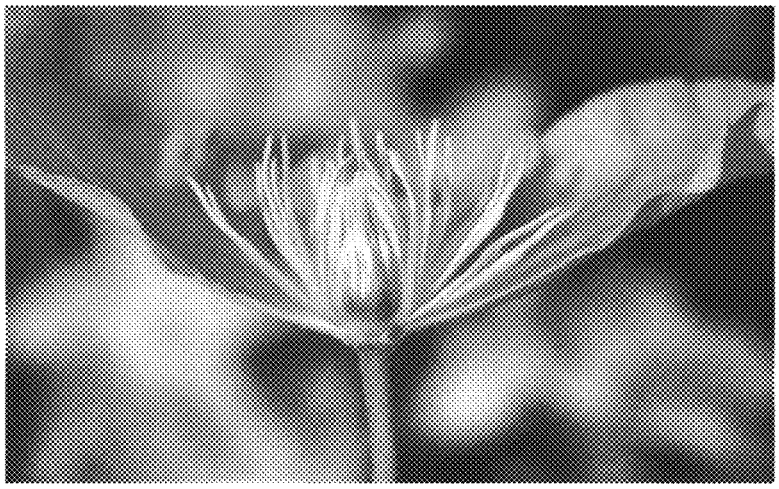

The photograph in FIG. 3 provides a close-up view of a cross section of a flower of 'Zo08160'.

The colors of the photographs are as close as possible with the digital photography techniques available, the color values cited in the detailed botanical description accurately describe the colors of the new *Clematis*.

DETAILED BOTANICAL DESCRIPTION

The following is a detailed description of two-year-old plants as grown outdoors in 2-Liter rose containers in Boskoop, The Netherlands. The phenotype of the new cultivar may vary with variations in environmental, climatic and cultural conditions, as the cultivar has not been tested under all possible environmental conditions. The color determination is in accordance with The 2015 Colour Chart of The Royal Horticultural Society, London, England, except where general color terms of ordinary dictionary significance are used.

General description:

*Blooming period.*—4 to 6 weeks in spring and throughout summer when pruned after spring flowering in The Netherlands.

*Plant type.*—Deciduous woody perennial, blooms on new shoots and old wood.

*Plant habit.*—Low growing climber.

*Height and spread.*—A three-year-old plant reaches an average of 2 m in height and 0.75 m in width.

*Cold hardiness.*—At least to U.S.D.A. Zone 6.

*Diseases and pests.*—No disease or pest problems have been observed, however susceptibility to *Clematis* wilt (caused by *Phoma* sp.)

*Root description.*—Fleshy, N167C and NN155D in color.

*Propagation.*—Softwood stem cuttings.

*Time required for root initiation.*—Roots develop in 6 weeks in summer under greenhouse conditions.

*Time required for root development.*—90 days to fully develop a 7-cm container from a 5 cm cutting.

*Growth rate.*—Moderate.

Stem description:

*Shape.*—Round with 6 ribbed angles.

*Stem color.*—Young; N77B, mature; 166A to 187A.

*Stem size.*—Up to 2 m in length, 3 mm in width.

*Stem surface.*—Young; densely pubescent, villous at the tip, mature; sparsely pubescent with short hairs.

*Internode length.*—Up to 11 cm.

*Strength.*—Strong and slightly flexible, cracks at a 25° angle.

*Branching.*—From the base.

Foliage description:

*Leaf arrangement.*—Opposite.

*Leaf division.*—Ternate.

*Leaf size.*—Up to 18 cm in length and 14 cm in width.

*Leaf attachment.*—Petiolate.

*Leaf fragrance.*—None.

*Leaflet shape.*—Ovate.

*Leaflet size.*—Up to 7 cm in length, up to 4 cm in width.

*Leaflet base.*—Side leaflets; suboblique, terminal leaflets; subcordate.

*Leaflet apex.*—Acuminate.

*Leaflet venation.*—Slightly reticulate, both surfaces match leaf color.

*Leaflet quantity.*—3.

*Leaflet margin.*—Entire.

*Leaflet surface.*—Upper surface; sparsely hairy, veins densely covered with short hairs, lower surface; glossy and densely covered with short hairs.

*Leaf color.*—Young upper and lower surface; 146B, mature upper surface; 147A, mature lower surface; 147B.

*Petioles.*—Up to 9 cm in length, 1.5 mm in diameter, N37C and N77A in color, round and slightly canaliculate in shape, curled to straight aspect, just slightly connate by means of ribs from the petiole that touch each other on the stem base, surface pubescent.

*Petiolules.*—Rounded in shape, 137C in color, curling to straight, terminal leaflet up to 4 cm in length, side leaflets up to 1 cm in length, 1 mm in diameter, surface pubescent.

Inflorescence description:

*Inflorescence type.*—Solitary or a 3-flowered dichasial cyme.

*Inflorescence arrangement.*—Terminal and axillary on young shoots.

*Inflorescence size.*—Up to 15 cm in length, 15 cm in width and 5 cm in depth when a 3-flowered cyme.

*Peduncles.*—Up to 4 mm in length and 2 mm in width, 146A and 166A in color, round to very slightly ribbed in shape, surface pubescent, strong.

*Pedicels.*—Up to 8 cm in length, 2 mm in diameter, 146D, tinged N77A in color, round in shape, surface pubescent, strong.

*Flower buds.*—Upright, ovate in shape, acuminate apex, obtuse base, up to 5 cm in length and 1.7 cm in diameter, 143D, slightly tinged N77B, surface densely pubescent; less towards the base with villous seams.

*Flower fragrance.*—None.

*Lastingness of the flowers.*—Individual flowers last up to 7 days.

*Flower quantity.*—Average of 50 flowers per plant 3 years in age.

*Flower type.*—Spreading.

*Flower aspect.*—Upright.

*Flower shape.*—Round and slightly star-shaped.

*Flower size.*—Up to 10 cm in diameter and 2 cm in depth.

*Flower sex.*—Bisexual.

*Receptacle.*—146B in color and 4 mm in diameter.

*Bracts.*—Simple, lanceolate in shape, up to 4 cm in length and 2 cm in width, acute apex, margins are entire, cuneate base, venation is reticulate, both surfaces sparsely pubescent and slightly glossy, color; upper surface 146A, lower surface 146B.

*Tepal number.*—8 on spring flowers, 6 on summer flowers.

*Tepal shape.*—Broadly elliptic to ovate.

*Tepal aspect.*—Flat and overlapping.

*Tepal apex.*—Acute to acuminate.

*Tepal base.*—Cuneate.

*Tepal margin.*—Entire, spring flowers distinctly wavy, summer flowers short wavy.

*Tepal surface.*—Upper surface; glabrous, lower surface; pubescent and almost velvety, center is densely pubescent.

*Tepal color.*—Spring flowers upper and lower surface when opening and fully open; 93D, 94C, N88D tinged 77B in the middle near the base, summer flowers upper and lower surface when opening and fully open; 92B and 155C in the middle towards the base.

*Tepal size.*—Up to 5 cm in length and an average of 3.5 cm in width.

*Petaloid staminodes.*—None Present.

Reproductive organs:

*Gynoecium.*—Covered by outer stamens, average of 50 pistils, up to 1 cm in length, ovary; 143C in color and pubescent, style; NN155A in color, plumose up to ⅔, upper ⅓ glabrous, stigma; straight to slightly bent in aspect, 145D in color, glabrous surface.

*Androecium.*—75 to 100, filaments; up to 1.1 cm in length, 1 mm in width and linear in shape, surface is glabrous, 145D in color, anthers; 6 mm in length, 1 mm in width, linear in shape, and 145D in color, glabrous surface, pollen; 4D in color and abundant in quantity, connective; straight in aspect, surface is glabrous and 145B in color, tip tinged N186A in color.

*Seed.*—Seed head; up to 4 cm in diameter, half orbicular in shape, 50% of the pistils might set seed by open pollination, seed; average of 25 per seed head, 4 mm in length and width, 71A, strongly tinged 144B in color, pubescent, seed style; up to 2 cm in length, 144B in color, surface 164D in color, seed stigma; thin and 200A in color.

It is claimed:

1. A new and distinct cultivar of *Clematis* plant named 'Zo08160' as herein illustrated and described.

* * * * *